(12) United States Patent
Lochead et al.

(10) Patent No.: US 8,211,903 B2
(45) Date of Patent: Jul. 3, 2012

(54) SUBSTITUTED PYRIMIDO ISOQUINOLINE DERIVATIVES

(75) Inventors: Alistair Lochead, Paris (FR); Mourad Saady, Paris (FR); Philippe Yaiche, Paris (FR)

(73) Assignees: Mitsubishi Tanabe Pharma Corporation, Osaka (JP); Sanofi-Aventis, Paris (FR)

( * ) Notice: Subject to any disclaimer, the term of this patent is extended or adjusted under 35 U.S.C. 154(b) by 0 days.

(21) Appl. No.: 12/968,950

(22) Filed: Dec. 15, 2010

(65) Prior Publication Data

US 2011/0144138 A1      Jun. 16, 2011

Related U.S. Application Data

(63) Continuation of application No. PCT/IB2009/006460, filed on Jun. 25, 2009.

(30) Foreign Application Priority Data

Jun. 26, 2008 (EP) .................... 08290618

(51) Int. Cl.
*A01N 43/54* (2006.01)
*A61K 31/505* (2006.01)
*C07D 239/70* (2006.01)
*C07D 471/00* (2006.01)

(52) U.S. Cl. ................. 514/267; 544/249
(58) Field of Classification Search .......... 514/267; 544/249

See application file for complete search history.

(56) References Cited

U.S. PATENT DOCUMENTS

| | | | |
|---|---|---|---|
| 4,104,386 A | 8/1978 | Barreau et al. | |
| 4,406,897 A | 9/1983 | Campbell et al. | |
| 4,461,769 A | 7/1984 | Hermecz et al. | |
| 4,804,663 A | 2/1989 | Kennis et al. | |
| 7,378,424 B2 * | 5/2008 | Oxford et al. | 514/267 |
| 2005/0009843 A1 | 1/2005 | Nakayama et al. | |
| 2011/0136828 A1 | 6/2011 | Lochead et al. | |
| 2011/0144092 A1 | 6/2011 | Fayol et al. | |
| 2011/0144114 A1 | 6/2011 | Lochead et al. | |
| 2011/0144132 A1 | 6/2011 | Fayol et al. | |
| 2011/0144133 A1 | 6/2011 | Lochead et al. | |

FOREIGN PATENT DOCUMENTS

| | | |
|---|---|---|
| DE | 2705582 | 8/1977 |
| EP | 1136484 | 9/2001 |
| EP | 1454909 | 9/2004 |
| EP | 1460076 | 9/2004 |
| EP | 1790649 | 5/2007 |
| FR | 2413389 | 7/1979 |
| JP | 51070780 | 6/1976 |
| WO | WO 96/14844 | 5/1996 |
| WO | WO 97/16430 | 5/1997 |
| WO | WO 98/47876 | 10/1998 |
| WO | WO 02/087589 | 11/2002 |
| WO | WO 03/027115 | 4/2003 |
| WO | WO 2004/016607 | 2/2004 |
| WO | WO 2007/057790 | 5/2007 |

OTHER PUBLICATIONS

U.S. Appl. No. 12/968,927, filed Dec. 15, 2010, Almario Garcia, et al.
Pyrimido [1.2-a] Benzimidazol-4(10H)-one, 2-(4-Pyridinyl)-, Database Accession No. RN 950257-17-7 ON: kcd-815548; abstract Aurora Screening Library (2008).
Bhat, R.V., et al., Glycogen Synthase Kinase 3: A Drug Target for CNS Therapies, Journal of Neurochemistry, vol. 89, pp. 1313-1317 (2004).
Carmichael, et al., Glycogen Synthase Kinase-3B Inhibitors Prevent Cellular Polyglutamine Toxicity Caused by the Huntington's Disease Mutation, The Journal of Biological Chemistry, 2002 (277)37 pp. 33791-33798.
Cohen, et al., GSK3 inhibitors: Development and Therapeutic Potential, Nature Reviews, 2004 (3) pp. 479-487.
Droucheau, et al., Plasmodium Falciparum Glycogen Synthase Kinase-3: Molecular Model, Expression, Intracellular Localisation and Selective inhibitors, Biochimica et Biophysica Acta, 2004 (1697) pp. 181-196
Dunbar, P. G., et al., Design, Synthesis and Neurochemical Evaluation of 2-Amino-5-(Alkoxycarbonyl)-3,4,5,6-Tetrahydropyridines and 2-Amino-6-(Alkoxycarbonyl)-1,4,5,6-Tetrahydropyrimidines as M1 Muscarinic Receptor Agonists, J. Med. Chem., (1994), vol. 37, pp. 2774-2782.
Griffin, R. J., et al., Selective Benzopyranone and Pyrimido[2,1-a]isoquinolin-4-one inhibitors of DNA-Dependent Protein Kinase: Synthesis, Structure-Activity Studies, and Radiosensitization of a Human Tumor Cell Line in Vitro, J. Med. Chem., (2005), vol. 48, pp. 569-585.
Hansen, D. W., et. al., 2,-Iminohomopiperidinium Salts as Selective inhibitors of Inducible Nitric Oxide Synthase (INOS), J. Med. Chem., (1998), vol. 41, pp. 1361-1366.
Ishikawa, et al., Cyclic Guanidines IX.1) Synthesis of 2-Amino-3,4-Dihydroquinazolines as Blood Platelet Aggregation Inhibitors 2), Chem. Pharm. Bull. vol. 28, No. 5, pp. 1357-1364, (1980).
Katritzky, A. R., et al., Convenient Preparation of Tert-Butyl B-(Protected Amino)Esters, J. Org. Chem., (2002), vol. 67, pp. 4957-4959.

(Continued)

*Primary Examiner* — Andrew D Kosar
*Assistant Examiner* — Erich A Leeser
(74) *Attorney, Agent, or Firm* — Kelly L. Bender

(57) ABSTRACT

Pyrimido isoquinoline derivatives represented by formula (I):

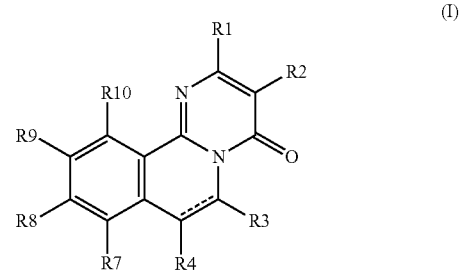

wherein:
R1, R2, R3, R4, R7, R8, R9, R10, and ⟿ are as defined in the disclosure. Also disclosed are methods of preparing the compounds of formula (I) and their use in therapeutics.

6 Claims, No Drawings

OTHER PUBLICATIONS

Kihara, et al., Reaction of Biguanides and Related Compounds. XVI. Synthesis of s-Triazinones and Fused s-Triazinones by Carbonylation of Biguanides and Related Compounds With Diethyl Azodicarboxylate, J. Heterocyclic Chem., vol. 27, pp. 1213-1216, (1990).

Kim, et al., Novel GSK-3B Inhibitors From Sequential Virtual Screening, Bioorganic & Medicinal Chemistiy, vol. 16, 2008, pp. 636-643.

Koh, et al., Role of GSK-3B Activity in Motor Neuronal Cell Death Induced by G93A or A4V Mutant HSOD1 Gene, European Journal of Neuroscience, 2005 (22) pp. 301-309.

Li, C., et al., Pyridine Derivatives as Potent inducers of Erythroid Differentiation in Friend Leukemia Cells, Journal of Medicinal Chemistry, vol. 21, No. 9, (1978). pp. 874-877.

Martinez, et al., Glycogen Synthase Kinase 3 (GSK-3) Inhibitors as New Promising Drugs for Diabetes, Neurodegeneration, Cancer, and Inflammation, Med. Res. Rev., 2002 (22)4 pp. 373-384.

Meijer, et al., Pharmacological Inhibitors of Glycogen Synthase Kinase 3, Trends in Pharmacological Sciences, 2004 (25)9 pp. 471-480.

Merour, et al., New Synthesis of (+/−)-2-Piperazinecarboxylic Acid, Tetrahedron Lett, 1991 (32) 22 pp. 2469-2470.

Murai, et al., Benzoguanides, Japanese Patent No.—JP 51070780—(ABSTRACT).

Obligado, et al., CDK/GSK-3 Inhibitors as Therapeutic Agents for Parenchymal Renal Diseases, Kidney Int'l, 2008 (73) pp. 684-690.

Perez, et al., Prion Peptide Induces Neuronal Cell Death Through a Pathway Involving Glycogen Synthase Kinase 3, Biochem. J., 2003 (372) pp. 129-136.

Sato, et al., Maintenance of Pluripotency in Human and Mouse Embryonic Stem Cells Through Activation of Wnt Signaling by a Pharmacological GSK-3-Specific Inhibitor, Nature Medicine, 2004 (10) pp. 55-63.

Thenappan, et al., An Expedient Synthesis of A-Fluoro-B-Ketoesters, Tetrahedron Letters, 1989 (30) 45 pp. 6113-6116.

Van Der Velden, J. L. J., et. al., Glycogen Synthase Kinase 3B Suppresses Myogenic Differentiation Through Negative Regulation of NFATc3, The Journal of Biological Chemistry, vol. 283. No. 1, pp. 358-366, (2008).

Von Angerer, et al., Product Subclass 3: 1,3,5-Triazines and Phosphorus Analogues, Science of Synthesis Catagory 2: Hetarenes and Related Ring Systems Six-Membered Hetarenes with Two Unlike or More Than Two Heteroatoms and Fully Unsaturated Larger-Ring Heterocycles: Methods of Molecular Transformations, vol. 17, (2004), pp. 449-583.

Woodgett, Use of Peptide Substrates for Affinity Purification of Protein-Serine Kinases, Analytical Biochemn., 1989 (180) pp. 237-241.

International Search Report for WO2009/156859 dated Dec. 30, 2009.

* cited by examiner

SUBSTITUTED PYRIMIDO ISOQUINOLINE DERIVATIVES

This application is a continuation of International Application No. PCT/IB2009/006460, filed Jun. 25, 2009, which is incorporated herein by reference in its entirety; which claims the benefit of priority of European Patent Application No. 08290618.1 filed Jun. 26, 2008.

TECHNICAL FIELD

The present invention relates to compounds that are useful as an active ingredient of a medicament for preventive and/or therapeutic treatment of neurodegenerative diseases caused by abnormal activity of GSK3β.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several tauopathies.

Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as p53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases and other pathologies where GSK3β is deregulated (Nature reviews Vol. 3, Jun. 2004, p. 479-487; Trends in Pharmacological Sciences Vol. 25 No. 9, Sept. 2004, p. 471-480; Journal of neurochemistry 2004, 89, 1313-1317; Medicinal Research Reviews, Vol. 22, No. 4, 373-384, 2002).

The neurodegenerative diseases include, in a non-limiting manner, Parkinson's disease, tauopathies (e.g. Fronto temporal dementia, corticobasal degeneration, Pick's disease, progressive supranuclear palsy), Wilson's disease, Huntington's disease (The Journal of biological chemistry Vol. 277, No. 37, Issue of Sept. 13, pp. 33791-33798, 2002), Prion disease (Biochem. J. 372, p. 129-136, 2003) and other dementia including vascular dementia; acute stroke and other traumatic injuries; cerebrovascular accidents (e.g. age related macular degeneration); brain and spinal cord trauma; amyotrophic lateral sclerosis (European Journal of Neuroscience, Vol. 22, pp. 301-309, 2005) peripheral neuropathies; retinopathies and glaucoma. Recent studies have also shown that inhibition of GSK3β results in neuronal differentiation of embryonic stem cells (ESC) and support the renewal of human and mouse ESCs and the maintenance of their pluripotency. This suggests that inhibitors of GSK3β could have applications in regenerative medicine (Nature Medicine 10, p. 55-63, 2004).

Inhibitors of GSK3β may also find application in the treatment of other nervous system disorders, such as bipolar disorders (manic-depressive illness). For example lithium has been used for more than 50 years as a mood stabilizer and the primary treatment for bipolar disorder. The therapeutic actions of lithium are observed at doses (1-2 mM) where it is a direct inhibitor of GSK3β. Although the mechanism of action of lithium is unclear, inhibitors of GSK3β could be used to mimic the mood stabilizing effects of lithium. Alterations in Akt-GSK3β signaling have also been implicated in the pathogenesis of schizophrenia.

In addition, inhibition of GSK3β could be useful in treating cancers, such as colorectal, prostate, breast, non-small cell lung carcinoma, thyroid cancer, T or B-cell leukaemia and several virus-induced tumours. For example, the active form of GSK3β has been shown to be elevated in the tumors of colorectal cancer patients and inhibition of GSK3β in colorectal cancer cells activates p53-dependent apoptosis and antagonizes tumor growth. Inhibition of GSK3β also enhances TRAIL-induced apoptosis in prostate cancer cell lines. GSK3β also plays a role in the dynamics of the mitotic spindle and inhibitors of GSK3β prevent chromosome movement and lead to a stabilization of microtubules and a prometaphase-like arrest that is similar to that observed with low doses of Taxol. Other possible applications for GSK3β inhibitors include therapy for non-insulin dependent diabetes (such as diabetes type II), obesity and alopecia.

Inhibitors of human GSK3β may also inhibit pfGSK3, an ortholog of this enzyme found in *Plasmodium falciparum*, as a consequence they could be used for the treatment of malaria (Biochimica et Biophysica Acta 1697, 181-196, 2004).

Recently, both human genetics and animal studies have pointed out the role of Wnt/LPR5 pathway as a major regulator of bone mass accrual. Inhibition of GSK3β leads to the consequent activation of canonical Wnt signaling. Because deficient Wnt signaling has been implicated in disorders of reduced bone mass, GSK3β inhibitors may also be used for treating disorders of reduced bone mass, bone-related pathologies, osteoporosis.

According to recent data, GSK3β inhibitors might be used in the treatment or prevention of *Pemphigus vulgaris*.

Recent studies show that GSK3beta inhibitor treatment improves neutrophil and megakaryocyte recovery. Therefore, GSK3beta inhibitors will be useful for the treatment of neutropenia induced by cancer chemotherapy.

Previous studies have shown that GSK3 activity decreases LTP, a electrophysiological correlate of memory consolidation, suggesting that inhibitor of this enzyme may have procognitive activity. Procognitive effects of the compound could find application for the treatment of memory deficits characteristic of Alzheimer's disease, Parkinson disease, age-associated memory impairment, mild cognitive impairment, brain trauma, schizophrenia and other conditions in which such deficits are observed.

Inhibitors of GSK3β may also find application in the treatment of parenchymal renal diseases (Nelson P J, Kidney International Advance online publication 19 Dec. 2007) and in the prevention or treatment of muscle atrophy (J. Biol. Chem. (283) 2008, 358-366).

DISCLOSURE OF THE INVENTION

An object of the present invention is to provide compounds useful as an active ingredient of a medicament for preventive and/or therapeutic treatment of a disease caused by abnormal GSK3β activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases.

The present invention thus provides as an object of the invention the pyrimidone derivatives represented by formula (I) or salts thereof, solvates thereof or hydrates thereof:

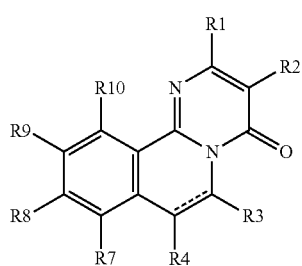

(I)

wherein:
R1 represents a 4-pyridine ring or a 4-pyrimidine ring
R2 represents a hydrogen atom;
R3 represents a hydrogen atom;
R4 represents a hydrogen atom or a halogen atom;
R7, R8, R9, R10 represent independently from each other a hydrogen atom, a halogen atom, a $C_{1-6}$ alkoxy group, a nitro, a hydroxyl, or an amino;

⋰⋰ represents a single or a double bond, in form of a free base or of an addition salt with an acid.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the present invention, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as:

Non-insulin dependent diabetes (such as diabetes type II) and obesity; malaria, bipolar disorders (manic depressive illness); schizophrenia; alopecia or cancers such as colorectal, prostate, breast cancer, non-small cell lung carcinoma, thyroid cancer, T or B-cell leukaemia, several virus-induced tumours and bone related pathologies; the treatment of parenchymal renal diseases and in the prevention or treatment of muscle atrophy; the treatment of cognitive and memory deficit. The medicament could also find an application in regenerative medicine.

As further embodiments of the present invention, there are provided the aforementioned medicament wherein the diseases are neurodegenerative diseases and are selected from the group consisting of Alzheimer's disease, Parkinson's disease, tauopathies (e.g. Fronto temporal dementia, corticobasal degeneration, Pick's disease, progressive supranuclear palsy), Wilson's disease, Huntington's disease, Prion disease and other dementia including vascular dementia; acute stroke and others traumatic injuries; cerebrovascular accidents (e.g. age related macular degeneration); brain and spinal cord trauma; amyotrophic lateral sclerosis; peripheral neuropathies; retinopathies and glaucoma, and the aforementioned medicament in the form of pharmaceutical composition containing the above substance as an active ingredient together with one or more pharmaceutical additives.

As further embodiments of the present invention, there are provided the aforementioned medicament wherein the bones related pathologies are osteoporosis. The present invention further provides an inhibitor of GSK3β activity comprising as an active ingredient a substance selected from the group consisting of the pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β activity, which comprises the step of administering to a patient a preventively and/or therapeutically effective amount of a substance selected from the group consisting of pyrimidone derivatives of formula (I) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched or cyclo alkyl group having 1 to 6 carbon atoms, optionally substituted by a straight, branched or cyclic $C_{1-6}$ alkyl group, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, cyclopropylmethyl group and the like.

The $C_{2-12}$ dialkylamino group represents an amino group substituted by two $C_{1-6}$ alkyl groups, for example, dimethylamino group, ethylmethylamino group, diethylamino group, methylpropylamino group and diisopropylamino group and the like;

In

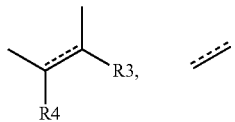

represents a single or a double bond. As used herein, when ⟿ represents a single bond, then there are hydrogen atoms attached to the carbon atoms adjacent to R3 and R4.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine and arginine. The base-addition salts of acidic compounds are prepared by standard procedures well known in the art.

When a basic group exists, examples include salts with mineral acids such as hydrochloric acid, hydrobromic acid; salts with organic acids such as acetic acid, propionic acid, tartaric acid, fumaric acid, maleic acid, malic acid, oxalic acid, succinic acid, citric acid, benzoic acid and the like.

The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the pyrimidone derivatives represented by the aforementioned formula (I) and salts thereof, their solvates and hydrates also fall within the scope of the present invention.

The pyrimidone derivatives represented by the aforementioned formula (I) may have one or more asymmetric carbon atoms. As for the stereochemistry of such asymmetric carbon atoms, they may independently be either in (R) or (S) configuration, and the derivative may exist as stereoisomers such as optical isomers, or diastereoisomers. Any stereoisomers in pure form, any mixtures of stereoisomers, racemates and the like fall within the scope of the present invention.

In a first embodiment of the invention, the compounds of the present invention are represented by formula (I)

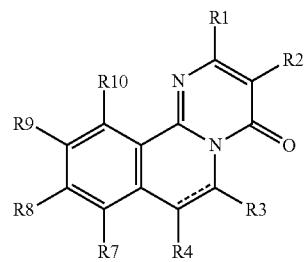

wherein:

R1 represents a 4-pyridine ring or a 4-pyrimidine ring;

R2 represents a hydrogen atom;

R3 represents a hydrogen atom;

R4 represents a hydrogen atom;

R7, R8, R9, R10 represent independently from each other a hydrogen atom, a halogen atom, a $C_{1-6}$ alkoxy group, a nitro, a hydroxyl or an amino;

⟿ represents a single or a double bond, in form of a free base or of an addition salt with an acid.

Examples of compounds of the present invention are shown in table 1 and in table 2 hereinafter. However, the scope of the present invention is not limited by these compounds. The nomenclature is given according to IUPAC rules. and compounds of table 1.

1. 2-Pyridin-4-yl-pyrimido[2,1-a]isoquinolin-4-one
2. 10-Bromo-2-pyridin-4-yl-pyrimido[2,1-a]isoquinolin-4-one
3. 10-Methoxy-2-pyridin-4-yl-pyrimido[2,1-a]isoquinolin-4-one
4. 8-Nitro-2-pyridin-4-yl-pyrimido[2,1-a]isoquinolin-4-one
5. 8-Amino-2-pyridin-4-yl-pyrimido[2,1-a]isoquinolin-4-one
6. 10-Hydroxy-2-pyridin-4-yl-pyrimido[2,1-a]isoquinolin-4-one
7. 10-Methoxy-2-pyrimidin-4-yl-pyrimido[2,1-a]isoquinolin-4-one
8. 2-Pyridin-4-yl-6,7-dihydro-pyrimido[2,1-a]isoquinolin-4-one
9. 9,10-Dimethoxy-2-pyridin-4-yl-6,7-dihydro-pyrimido[2,1-a]isoquinolin-4-one As a further object, the present invention concerns also methods for preparing the pyrimidone compounds represented by the aforementioned formula (I). These compounds can be prepared, for example, according to methods explained below.

Preparation Method:

Pyrimidone compounds represented by the aforementioned formula (I), may be prepared according to the method described in the scheme 1 when

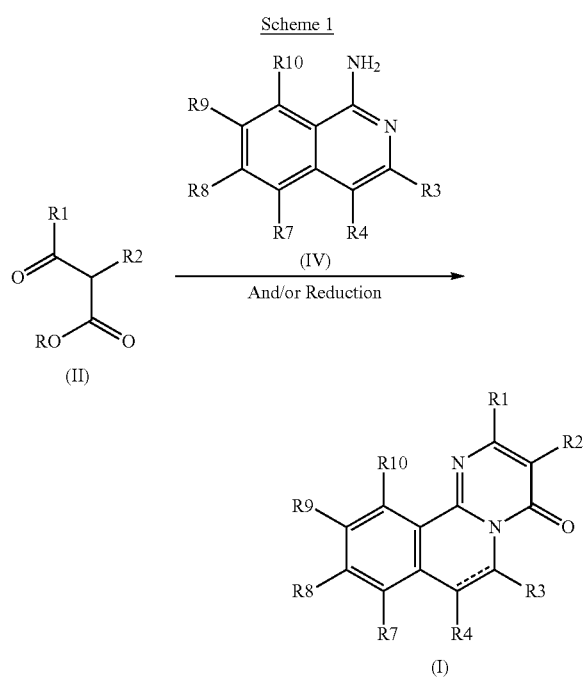

Scheme 1

(In the above scheme the definition of R1 to R10 are the same as those already described for compound of formula (I)).

Compounds of formula (II) and (IV) are commercially available or may be synthesized according to well-known methods to one skilled in the art.

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, tauopathies (e.g. Fronto temporal dementia, corticobasal degeneration, Pick's disease, progressive supranuclear palsy), Wilson's disease, Huntington's disease, Prion disease and other dementia including vascular dementia; acute stroke and others traumatic injuries; cerebrovascular accidents (e.g. age related macular degeneration); brain and spinal cord trauma; amyotrophic lateral sclerosis, peripheral neuropathies; retinopathies and glaucoma; and other diseases such as non-insulin dependent diabetes (such as diabetes type II) and obesity; malaria, manic depressive illness; schizophrenia; alopecia; cancers such as colorectal, prostate breast cancer, non-small cell lung carcinoma, thyroid cancer, T or B-cell leukemia, several virus-induced tumours and in bone related pathologies; parenchymal renal diseases or muscle atrophy. The medicament could also find an application in regenerative medicine. The medicament could also find an application in the treatment or prevention of *Pemphigus vulgaris*. The medicament could also find an application in the treatment of neutropenia induced by cancer chemotherapy. The medicament could also find an application for therapeutic treatment of a disease characterized by cognitive and memory deficits such as in Alzheimer's disease, Parkinson disease, age associated memory impairment, mild cognitive impairment, brain trauma, schizophrenia and other conditions in which such deficits are observed.

The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention; however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

Example 1

Compound No. 2 of Table 1

10-Bromo-2-pyridin-4-yl-4H-pyrimido[2,1-a]iso-quinolin-4-one oxalate (1:1)

To a mixture of 0.1 g (0.38 mmol) of 7-bromoisoquinolin-1-amine (synthesis described in WO9847876) and 0.134 g (0.69 mmol) of ethyl 3-(4-pyridinyl)-3-oxopropionate were added 0.059 g (0.77 mmol) of ammonium acetate. The reaction mixture was heated at 140° C. for 12 hours. Then 2 ml of Dowtherm A were added and the resulting mixture was allowed to stir at 210° C. for 8 hours. After cooling, water was added and the resulting solution was acidified using isopropanol hydrochloride 6N. Dowtherm A was extracted using diethyl ether and the aqueous phase was basified by an aqueous solution of sodium hydroxide (30%) and extracted with dichloromethane. The extracts were dried over sodium sulphate and evaporated. The residue obtained was purified by chromatography on silica gel eluting with a mixture of dichloromethane/methanol in the proportions 99/1 to 95/5 to give 0.041 g (30%) of the desired compound which was transformed into the oxalate salt in the usual manner to give the pure product as a solid.

MP: 244-246° C.

RMN $^1$H (DMSO-d$^6$; 200 MHz)

δ (ppm): 9.25 (s, 1H), 8.80 (d, 2H), 8.70 (d, 1H), 8.30 (d, 2H), 8.10 (dd, 1H), 8.00 (dd, 1H), 7.65 (d, 1H), 7.40 (s, 1H).

Example 2

Compound No. 3 of Table 1

10-methoxy-2-pyridin-4-yl-4H-pyrimido[2,1-a]iso-quinolin-4-one maleate (1:1)

By analogy with the method described in example 1, using 7-methoxyisoquinolin-1-amine (synthesis described in WO9847876) in place of 7-bromoisoquinolin-1-amine to afford the product which was transformed into the maleate salt in the usual manner to give 0.22 g (16%) of a solid.

Mp: 260-262° C.

RMN $^1$H (DMSO-d$^6$; 200 MHz)

δ (ppm): 9.20 (d, 2H), 9.00 (d, 2H), 8.75 (d, 1H), 8.55 (d, 1H), 8.00 (d, 1H), 7.60 (m, 3H), 4.00 (s, 3H).

Example 3

Compound No. 8 of Table 1

2-Pyridin-4-yl-6,7-dihydro-pyrimido[2,1-a]isoquinolin-4-one oxalate (1:1)

4.1 2-Pyridin-4-yl-pyrimido[2,1-a]isoquinolin-4-one

By analogy with the method described in example 1, using isoquinolin-1-amine (synthesis described in WO9847876) in place of 7-bromoisoquinolin-1-amine to afford the product as a free base to give 1.0 g (13%) of a solid which was used as such for the next step.

4.2 2-Pyridin-4-yl-6,7-dihydro-pyrimido[2,1-a]iso-quinolin-4-one oxalate (1:1)

To a solution of 0.20 g (0.73 mmol) of 2-pyridin-4-yl-pyrimido[2,1-a]isoquinolin-4-one in 15 ml of methanol was added 0.500 ml of a 6N solution of hydrochloric acid in isopropanol and 0.05 g of palladium on carbon catalyst (10% wt/wt).

The suspension was hydrogenated under 10 psi pressure at room temperature during 4 h.

The catalyst was removed by filtration and the solvent evaporated under reduced pressure. The resulting solid was dissolved in methanol and purified on preparative thin layer chromatography eluting with a mixture of dichloromethane/methanol/aqueous ammonia solution (29%) in the proportions 95/5/0.5 to afford 0.04 g (20%) of the compound as a free base which was transformed into the oxalate salt in the usual manner to give 0.02 g of a solid.

Mp: 255-257° C.

RMN $^1$H (DMSO-d$^6$; 200 MHz)

δ (ppm): 8.80 (br s, 2H), 8.50 (d, 1H), 8.15 (d, 2H), 7.80-7.40 (m, 3H), 7.15 (s, 1H), 4.20 (dd, 2H), 3.10 (dd, 2H).

A list of chemical structures and physical data for compounds of the aforementioned formula (Ib), illustrating the present invention, is given in table 2. The compounds of table 1 represent compounds of the present invention The compounds have been prepared according to the methods of the examples.

In the table, Me represents a methyl group, (Rot.) indicates the levorotatory or dextrorotatory properties of the enantiomeric compound, (dec.) indicates the decomposition of the compound; R2, R3 and R10 represent a hydrogen atom.

 represents a single or a double bond.

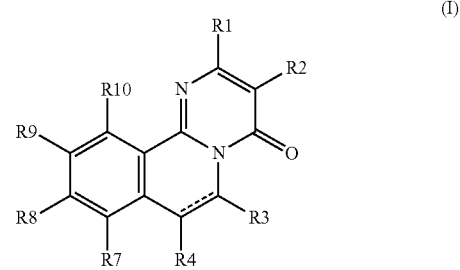

(I)

TABLE 1

| No. | R9 | R8 | R7 | R4 | R1 | bond | Mp °C | salt |
|---|---|---|---|---|---|---|---|---|
| 1 | H | H | H | H | pyridin-4-yl | Double bond | 260-261 | Oxalate 1:1 |
| 2 | Br | H | H | H | pyridin-4-yl | Double bond | 244-246 | Oxalate 1:1 |
| 3 | $CH_3O$ | H | H | H | pyridin-4-yl | Double bond | 260-262 | Oxalate 1:1 |
| 4 | H | H | $NO_2$ | H | pyridin-4-yl | Double bond | 270-272 | Hydrochloride 1:1 |
| 5 | H | H | $NH_2$ | H | pyridin-4-yl | Double bond | 329-331 | Free Base |
| 6 | OH | H | H | H | pyridin-4-yl | Double bond | 368-370 | Oxalate 1:1 |
| 7 | $CH_3O$ | H | H | H | pyrimidin-4-yl | Double bond | 302-304 | Free Base |
| 8 | H | H | H | H | pyridin-4-yl | Single bond | 255-257 | Oxalate (1:1) |
| 9 | OMe | OMe | H | H | pyridin-4-yl | Single bond | 271-273 | Free Base |

Test Example

Inhibitory Activity of the Medicament of the Present Invention Against GSK3β

Four different protocols can be used.

In a first protocol: 7.5 µM of prephosphorylated GS1 peptide and 10 µM ATP (containing 300,000 cpm of $^{33}$P-ATP) were incubated in 25 mM Tris-HCl, pH 7.5, 0.6 mM DTT, 6 mM $MgCl_2$, 0.6 mM EGTA, 0.05 mg/ml BSA buffer for 1 hour at room temperature in the presence of GSK3beta (total reaction volume: 100 microliters).

In a second protocol: 4.1 µM of prephosphorylated GS1 peptide and 42 µM ATP (containing 260,000 cpm $^{33}$P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3beta.

In a third protocol: 7.5 µM of prephosphorylated GS1 peptide and 10 µM ATP (containing 300,000 cpm of $^{33}$P-ATP) were incubated in 50 mM Hepes, pH 7.2, 1 mM DTT, 1 mM $MgCl_2$, 1 mM EGTA, 0.01% Tween 20 buffer for one hour at room temperature in the presence of GSK3beta (total reaction volume: 100 microliters).

In a fourth protocol: 7.5 µM of prephosphorylated GS1 peptide and 10 µM ATP (containing 300,000 cpm of $^{33}$P-ATP) were incubated in 50 mM Hepes, pH 7.2, 1 mM DTT, 1 mM $MgCl_2$, 1 mM EGTA, 0.01% Tween 20 buffer for 90 minutes at room temperature in the presence of commercial GSK3beta (Millipore) (total reaction volume: 100 microliters).

Inhibitors were solubilized in DMSO (final solvent concentration in the reaction medium, 1%).

The reaction was stopped with 100 microliters of a solution made of 25 g polyphosphoric acid (85% $P_2O_5$), 126 ml 85% $H_3PO_4$, $H_2O$ to 500 ml and then diluted to 1:100 before use. An aliquot of the reaction mixture was then transferred to Whatman P81 cation exchange filters and rinsed with the solution described above. Incorporated $^{33}$P radioactivity was determined by liquid scintillation spectrometry.

The phosphorylated GS-1 peptide had the following sequence: NH2-YRRAAVPPSPSLSRHSSPHQS(P)EDEE-COOH. (Woodgett, J. R. (1989) Analytical Biochemistry 180, 237-241.

The GSK3β inhibitory activity of the compounds of the present invention are expressed in $IC_{50}$, and as an illustration the range of $IC_{50}$'s of the compounds in table 1 and table 2 are between 30 nanomolar to 5 micromolar concentrations.

For example, on the protocol 3, the compound No. 1 of table 1 shows an $IC_{50}$ of 0.330 µM, the compound No. 5 of table 1 shows an $IC_{50}$ of 0.170 µM and compound No 12 of table 1 shows an $IC_{50}$ of 0.195 µM.

FORMULATION EXAMPLE (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

(3) Parenteral Preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

Industrial Applicability

The compounds of the present invention have GSK3β inhibitory activity and are useful as an active ingredient of a medicament for preventive and/or therapeutic treatment of diseases caused by abnormal activity of GSK3β and more particularly of neurodegenerative diseases.

What is claimed is:

1. A compound of formula (I):

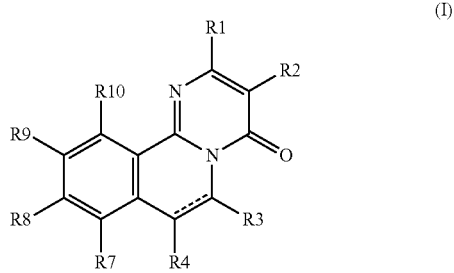

wherein:
R1 represents a 4-pyridine ring or a 4-pyrimidine ring;
R2 represents a hydrogen atom;
R3 represents a hydrogen atom;
R4 represents a hydrogen atom or a halogen atom;
R7, R8, R9, R10 represent independently from each other a hydrogen atom, a halogen atom, a $C_{1-6}$ alkoxy group, a nitro, a hydroxyl or an amino; and ⋯ represents a single or a double bond, wherein when ⋯ represents a single bond then there are hydrogen atoms attached to the carbon atoms adjacent to R3 and R4;
or an acid addition salt thereof.

2. The compound according to claim 1 of formula (I):

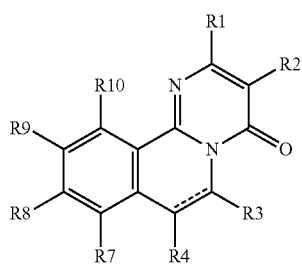

wherein:
R1 represents a 4-pyridine ring or a 4-pyrimidine ring;
R2 represents a hydrogen atom;
R3 represents a hydrogen atom;
R4 represents a hydrogen atom;
R7, R8, R9, R10 represent independently from each other a hydrogen atom, a halogen atom, a $C_{1-6}$ alkoxy group, a nitro, a hydroxyl or an amino; and ⋯ represents a single or a double bond, wherein when ⋯ represents a single bond then there are hydrogen atoms attached to the carbon atoms adjacent to R3 and R4;
or an acid addition salt thereof.

3. The compound according to claim 1 selected from the group consisting of:

2-Pyridin-4-yl-pyrimido[2,1-a]isoquinolin-4-one;

10-Bromo-2-pyridin-4-yl-pyrimido[2,1-a]isoquinolin-4-one;

10-Methoxy-2-pyridin-4-yl-pyrimido[2,1-a]isoquinolin-4-one;

8-Nitro-2-pyridin-4-yl-pyrimido[2,1-a]isoquinolin-4-one;

8-Amino-2-pyridin-4-yl-pyrimido[2,1-a]isoquinolin-4-one;

10-Hydroxy-2-pyridin-4-yl-pyrimido[2,1-a]isoquinolin-4-one;

10-Methoxy-2-pyrimidin-4-yl-pyrimido[2,1-a]isoquinolin-4-one;

2-Pyridin-4-yl-6,7-dihydro-pyrimido[2,1-a]isoquinolin-4-one; and 9,10-Dimethoxy-2-pyridin-4-yl-6,7-dihydro-pyrimido[2,1-a]isoquinolin-4-one;

or an acid addition salt thereof.

4. A pharmaceutical composition comprising a compound of formula (I) according to claim 1 or a pharmaceutically acceptable salt thereof and one or more pharmaceutical additives.

5. A pharmaceutical composition comprising a compound of formula (I) according to claim 2 or a pharmaceutically acceptable salt thereof and one or more pharmaceutical additives.

6. A pharmaceutical composition comprising a compound according to claim 3 or a pharmaceutically acceptable salt thereof and one or more pharmaceutical additives.

* * * * *